United States Patent
Patel et al.

(10) Patent No.: US 10,980,647 B2
(45) Date of Patent: Apr. 20, 2021

(54) KNEE LIGAMENT BALANCER

(71) Applicant: Medtronic Advanced Energy, LLC, Minneapolis, MN (US)

(72) Inventors: Rajan Patel, Portsmouth, NH (US); Mark M. Guirguis, Union, NJ (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 289 days.

(21) Appl. No.: 16/158,040

(22) Filed: Oct. 11, 2018

(65) Prior Publication Data
US 2020/0113714 A1 Apr. 16, 2020

(51) Int. Cl.
*A61F 2/46* (2006.01)
*A61B 34/00* (2016.01)

(52) U.S. Cl.
CPC ............ *A61F 2/4657* (2013.01); *A61B 34/25* (2016.02); *A61F 2/4684* (2013.01); *A61F 2002/4666* (2013.01)

(58) Field of Classification Search
CPC ................ A61B 5/4585; A61B 5/6885; A61B 2090/065; A61F 2/4657; A61F 2/4684; A61F 2002/4666
See application file for complete search history.

(56) References Cited

U.S. PATENT DOCUMENTS

| 4,963,152 | A | 10/1990 | Hofmann et al. |
| 7,578,821 | B2 | 8/2009 | Fisher et al. |
| 7,628,818 | B2 | 12/2009 | Hazebrouck et al. |
| 8,211,041 | B2 * | 7/2012 | Fisher ...................... A61F 2/38 600/595 |
| 8,714,009 | B2 * | 5/2014 | Stein .................. A61B 17/1666 73/379.06 |
| 8,979,758 | B2 * | 3/2015 | Stein .................... A61B 5/4851 600/438 |
| 9,345,492 | B2 * | 5/2016 | Stein .................. A61B 17/1666 |
| 9,358,136 | B2 * | 6/2016 | Stein .................. A61B 5/6847 |
| 9,649,119 | B2 | 5/2017 | Rock et al. |
| 9,839,390 | B2 * | 12/2017 | Stein .................... A61F 2/4684 |
| 9,844,335 | B2 * | 12/2017 | Stein .................... A61B 5/4528 |
| 10,004,449 | B2 * | 6/2018 | Stein .................... A61B 5/4585 |
| 2003/0153978 | A1 | 8/2003 | Whiteside |
| 2004/0064191 | A1 * | 4/2004 | Wasielewski ......... A61F 2/4684 623/20.14 |

(Continued)

OTHER PUBLICATIONS

Optimum Flexion Gap and Ligament Balance, Design Rationale, Synvasive Technology, Inc., synvasive.com.

*Primary Examiner* — Eric S Gibson
(74) *Attorney, Agent, or Firm* — Fox Rothschild LLP

(57) ABSTRACT

An orthopedic surgical device and method of using thereof is provided. The orthopedic surgical device includes a sensor portion including a conformable pad sized for positioning within a knee joint of a patient. The pad includes a femoral side and a tibial side and a sensor array disposed between the femoral side and the tibial side configured to generate a signal indicative of the force within the knee joint. The tibial side includes an adhesive coating. The orthopedic surgical device also includes a display portion including a display and a controller. The controller is configured to receive the signal from the sensor array and to control the display to provide a visual indication of the force within the knee joint.

20 Claims, 4 Drawing Sheets

(56) References Cited

U.S. PATENT DOCUMENTS

| | | | |
|---|---|---|---|
| 2011/0319755 A1* | 12/2011 | Stein | A61F 2/4657 600/437 |
| 2012/0152036 A1* | 6/2012 | Stein | A61B 5/6847 73/862.626 |
| 2012/0216611 A1* | 8/2012 | Stein | G01L 1/255 73/379.01 |
| 2013/0023794 A1* | 1/2013 | Stein | A61B 5/412 600/587 |
| 2013/0023795 A1* | 1/2013 | Stein | A61F 2/4657 600/587 |
| 2013/0204157 A1* | 8/2013 | Clark | G01G 23/3735 600/547 |
| 2013/0226034 A1* | 8/2013 | Stein | A61B 5/1036 600/587 |
| 2013/0226035 A1* | 8/2013 | Stein | A61B 5/4585 600/587 |
| 2013/0226036 A1* | 8/2013 | Stein | A61B 5/076 600/587 |
| 2013/0331850 A1 | 12/2013 | Bojarski et al. | |
| 2014/0094715 A1* | 4/2014 | Stein | G01L 5/16 600/587 |
| 2014/0135655 A1* | 5/2014 | Stein | A61F 2/4657 600/587 |
| 2014/0188117 A1* | 7/2014 | Stein | A61B 5/076 606/81 |
| 2014/0200584 A1* | 7/2014 | Stein | A61B 5/076 606/80 |
| 2014/0288464 A1* | 9/2014 | Stein | A61F 2/4657 600/595 |
| 2015/0238691 A1* | 8/2015 | Boyden | A61F 2/30 604/66 |
| 2020/0113714 A1* | 4/2020 | Patel | A61B 5/4585 |

\* cited by examiner

KNEE LIGAMENT BALANCER

TECHNICAL FIELD

The present disclosure generally relates to orthopedic medical devices, and more particularly, devices, systems, and methods for determining and displaying knee joint force data.

BACKGROUND

During total knee replacement surgeries, also known as total knee arthroplasty, portions of the femur and tibia are removed and replaced with artificial prosthetics, and an artificial bearing surface is placed between the femoral and tibial components. The shaping of the bone must be very precise to ensure that the tension in the knee ligaments, especially the medial collateral ligament and the lateral collateral ligament are balanced and the knee is stable and properly aligned throughout the complete range of motion of the knee.

Surgeons often employ non-permanent trial components in order to test the mobility and tightness of the knee. In particular, they are often looking at whether or not the knee is balanced, and if the ligaments are at the appropriate tension. This is generally assessed through feel and based on the experience of the surgeon. However, there can be serious negative repercussions from having improper ligament balancing. Improper soft tissue balancing and mal-alignment cause 40% of premature implant failures, and in many cases revision total knee surgery becomes necessary. Properly balanced knees lead to reduced post-operative pain, increased activity level, improved functional outcomes, and improved patient satisfaction.

In an effort to remove the qualitative aspect of this step, there are devices known as ligament balancers that attempt to quantify the force between the femoral component and the tibial component and/or other load information. However, these ligament balancers are often complex and implant specific. What is needed is a low-cost, universal ligament balancer.

The embodiments of the disclosure described herein seek to address these and other shortcomings in the existing art.

SUMMARY

In one aspect of the present disclosure, a low-cost, and therefore more practically disposable, orthopedic surgical device is provided for knee ligament balancing. In some embodiments, the orthopedic surgical device comprises a sensor portion including a conformable pad sized for positioning within a knee joint of a patient, wherein the pad includes a femoral side, a tibial side, and a sensor array disposed between the femoral side and the tibial side configured to generate a signal indicative of the force within the knee joint, wherein the tibial side includes an adhesive coating; and a display portion including a display and a controller, wherein the controller is configured to receive the signal from the sensor array and to control the display to provide a visual indication of the force within the knee joint.

In some embodiments, the orthopedic surgical device further comprises a connection wire between the sensor portion and the display portion configured to transmit the signal to the controller. In some embodiments, the connection wire comprises a connector such that the sensor portion is detachable from the display portion.

In some embodiments, the pad comprises a medical grade moldable plastic. In some embodiments, the medical grade moldable plastic is silicon. In other embodiments, the medical grade moldable plastic is polyurethane.

In some embodiments, the sensor array comprises a first sensor positioned laterally adjacent a second sensor. In some embodiments, when the pad is positioned within the knee joint of the patient, the first sensor is positioned to generate a first signal indicative of the force within the lateral compartment of the knee and the second sensor is positioned to generate a second signal indicative of the force within the medial compartment of the knee.

In some embodiments, the controller is further configured to receive the first signal from the first sensor to determine a first force value and the second signal from the second sensor to determine a second force value and to control the display to provide a first visualization mode wherein the first force value is displayed adjacent the second force value. In some embodiments, the controller is further configured to receive the first signal from the first sensor to determine a first force value and the second signal from the second sensor to determine a second force value and to control the display to provide a second visualization mode wherein a plot of the lateral force value and medial force value is displayed. In some embodiments, the display portion is configured to allow a user of the orthopedic surgical device to switch between the first visualization mode and the second visualization mode.

In some embodiments, the controller is further configured to receive the first signal from the first sensor to determine a first force value and the second signal from the second sensor to determine a second force value and to control the display to provide a first visualization mode wherein a plot of the first force value and second force value is displayed.

In some embodiments, the first sensor comprises a force sensitive resistor and the second sensor comprises a force sensitive resistor. In some embodiments, the first sensor comprises a circular, rectangular, or oval geometry, and the second sensor comprises a circular, rectangular, or oval geometry.

In some embodiments, the adhesive is an acrylate-based adhesive.

In some embodiments, the femoral side of the sensor portion is treated to increase lubricity compared to the tibial side of the sensor portion.

In another aspect, the present disclosure provides an orthopedic surgical device including a sensor portion includes a conformable pad sized for positioning within a knee joint of a patient, wherein the sensor portion comprises a femoral side, a tibial side, and a sensor array disposed between the femoral side and the tibial side, wherein the sensor array includes a first sensor positioned laterally adjacent a second sensor such that when the pad is positioned within the knee joint of the patient, the first sensor is positioned to generate a first signal indicative of the force within the lateral compartment of the knee and the second sensor is positioned to generate a second signal indicative of the force within the medial compartment of the knee, wherein the tibial side comprises an adhesive coating; a display portion including a display and a controller, wherein the controller is configured to receive the first signal from the first sensor to determine a first force value and the second signal from the second sensor to determine a second force value and to control the display to provide a first visualization mode and a second visualization mode and a visual button to switch between the first visualization mode and the second visualization mode, wherein in the first visualization mode, the first force value is displayed adjacent the second force value and in the second visualization mode, a plot of the lateral force value and medial force value is displayed; and a detachable connection wire between the sensor portion and the display portion configured to transmit the first signal and second signal to the controller.

In another aspect, the present disclosure provides a method for performing an orthopedic surgical procedure on a knee joint of a patient, the method comprising providing an orthopedic surgical device comprising a sensor portion including a conformable pad sized for positioning within a knee joint of a patient, wherein the sensor portion includes a femoral side, a tibial side, and a sensor array disposed between the femoral side and the tibial side, wherein the sensor array includes a first sensor positioned laterally adjacent a second sensor such that when the pad is positioned within the knee joint of the patient, the first sensor is positioned to generate a first signal indicative of the force within the lateral compartment of the knee and the second sensor is positioned to generate a second signal indicative of the force within the medial compartment of the knee, wherein the tibial side includes an adhesive coating; a display portion including a display and a controller, wherein the controller is configured to receive the first signal from the first sensor to determine a first force value and the second signal from the second sensor to determine a second force value and to control the display to provide a first visualization mode and a second visualization mode and a visual button to switch between the first visualization mode and the second visualization mode, wherein in the first visualization mode, the first force value is displayed adjacent the second force value and in the second visualization mode, a plot of the lateral force value and medial force value is displayed; and a detachable connection wire between the sensor portion and the display portion configured to transmit the first signal and second signal to the controller, adhering the tibial side of the pad to a component of a knee prosthesis system, inserting the component of the knee prosthesis system into the knee joint of the patient, and measuring the forces of the lateral compartment and the medial compartment, wherein the forces are displayed on the display of the orthopedic surgical device.

In some embodiments, the forces of the lateral compartment and the medial compartment are measured over the full range of motion of the knee joint of the patient. In some embodiments, the method further comprises performing a balancing procedure to adjust a mediolateral balance of the knee joint of the patient.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

DETAILED DESCRIPTION

The present disclosure provides devices, systems, and methods for enhancing orthopedic surgical procedures, and more particularly knee arthroplasty procedures. The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Terms representing anatomical references, such as anterior, posterior, medial, lateral, superior, inferior, etc., may also be used throughout this disclosure in reference both to a patient's anatomy or orthopedic devices discussed herein. Such terms have well-understood meanings in both the study of anatomy and the field of orthopedics. Use of such anatomical reference terms is intended to be consistent with their well-understood meanings unless otherwise noted.

Figure 1:
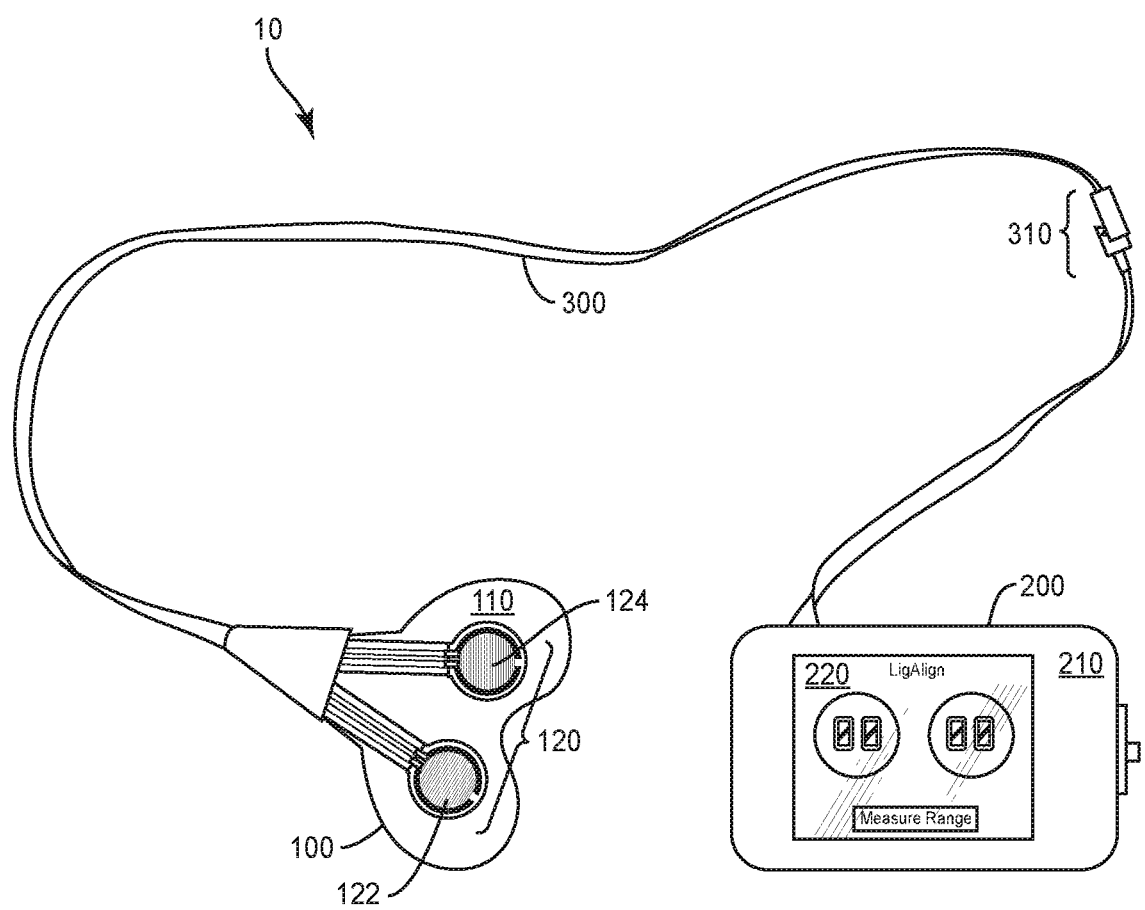
FIG. 1 is a perspective view of a representative knee ligament balancer in accordance with the principles of the present disclosure.

Referring now to FIG. 1, in one embodiment, an orthopedic surgical device 10 for determining and displaying the joint forces of a patient's knee during an orthopedic procedure on the knee, such as a partial or total knee arthroplasty procedure, to assist in ligament balancing is shown. The knee ligament balancer 10 comprises a sensor portion 100, a display portion 200, and a connection wire 300. As discussed in more detail below, sensor portion 100 is configured to be placed within the knee joint of a patient during a surgical procedure and provide a visual display of the joint forces to the orthopedic surgeon. In one embodiment, the knee ligament balancer 10 provides a visual indication of the joint forces within the lateral and medial compartments of the knee so that the orthopedic surgeon may perform appropriate ligament balancing procedures to provide a balanced knee.

In one embodiment, sensor portion 100 comprises a thin pad 110 in which a sensor array 120 has been disposed. The pad 110 may be comprised of multiple layers of material with the sensor array 120 disposed therebetween. In other embodiments, pad 110 may be formed using a variety of subtractive and additive manufacturing techniques, such as molding, and sensor array 120 may be disposed within pad 110 during this process.

The pad 110 may be made from a medical grade moldable plastic such that it is malleable and can conform to any surface. For example, as shown in FIG. 2B, sensor portion 100 has been adhered to a trial component of a knee prosthesis system and it can be seen how the sensor portion 100 has conformed to the particular shape of the chosen component. The malleability and conformability of the sensor portion 100 allows it to be used with a variety of different prosthetic systems. In this way, knee ligament balancer 100 is not limited to any particular implant and may be used universally because sensor portion 100 may be adapted to be used with any bearing surface and a variety of sizes. Pad 110 of sensor portion 100 may be made of any suitable non-rigid, malleable medical grade material as known to those of skill in the art. In some embodiments, pad 110 of sensor portion 100 may be made from silicon. In another embodiment, pad 110 of sensor portion 100 may be made from polyurethane.

Figure 2A:
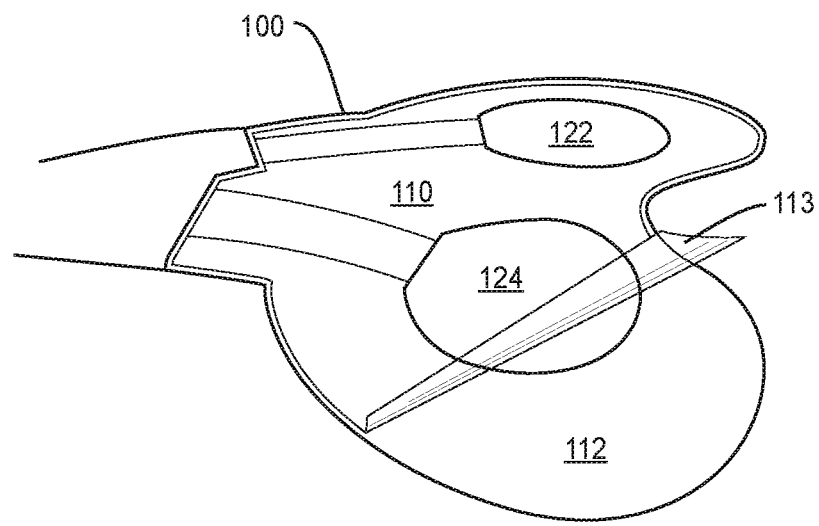
FIG. 2A illustrates a sensor portion of a representative knee ligament balancer before being attached to a component of a knee implant prosthesis in accordance with the principles of the present disclosure.
Figure 2B:
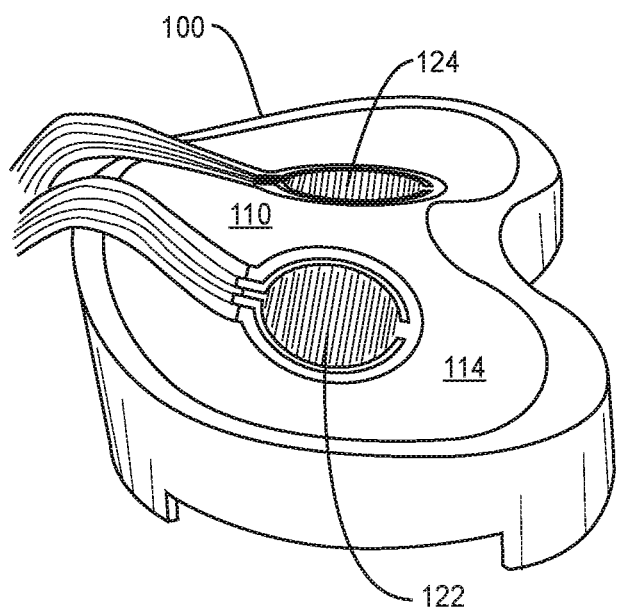
FIG. 2B illustrates a sensor portion of a representative knee ligament balancer after being attached to a component of a knee implant prosthesis in accordance with the principles of the present disclosure.

In some embodiments, pad 110 may have a tibial side 112, as shown in FIG. 2A, and a femoral side 114, as shown in FIG. 2B. The pad 110 is designed to be placed within a patient's knee joint such that tibial side 112 is oriented towards the patient's tibia, and femoral side 114 is oriented towards the patient's femur. Although pad 110 may be formed from a single material, tibial side 112 and femoral side 114 of pad 110 may be treated so that each surface is better suited to the particular requirements of the different surfaces of the knee joint. For instance, in a typical knee joint, the surfaces of the femoral condyle roll or slide over the surface of the tibial plateau as the knee if flexed and extended. Likewise, in a knee joint prosthesis, the distal end of the femoral component is designed to roll or slide over the bearing surface. With this in mind, femoral side 114 of pad 110 may be coated or treated to increase lubricity over that of tibial side 112 such that the friction between the femoral component of the knee prosthesis and pad 110 is reduced. By allowing the femoral component of the knee prosthesis to property track over pad 110 and eliminating any sticking, a more accurate force measurement may be obtained. In some embodiments, tibial side 112 may be coated or treated with an adhesive to secure the pad 110 to the trial component of the knee prosthesis. In this way, the position of the sensor portion 100 is stabilized to ensure that it does not displace during flexion or extension of the knee as the femoral component tracks over pad 110. In some embodiments, the adhesive is an acrylate-based adhesive. In some embodiments where tibial side 112 has been coated with adhesive, tibial side 112 may further comprise a peelable layer 113 to cover the adhesive until use.

In some embodiments, sensor array 120 may comprise a first sensor portion 122 and a second sensor 124 arranged laterally adjacent to each other such that when sensor portion 100 positioned within a knee joint, the first sensor 122 is positioned within the lateral compartment of the knee and the second sensor 124 is positioned within the medial compartment of the knee. Positioned in this way, first sensor 122 may generate a signal indicative of the force within the lateral compartment of the knee as it is flexed and extended, and second sensor 124 may generate a signal indicative of the force within the medial compartment of the knee as it is flexed and extended. However, as can be seen, sensor portion 100 may be laterally symmetrical such that sensor portion 100 may be placed within either knee joint of a patient. Accordingly, in some embodiments, the first sensor 122 is positioned within the medial compartment of the knee and the second sensor 124 is positioned within the lateral compartment of the knee and first sensor 122 and second sensor 124 measure the forces within those respective compartments.

First sensor 122 and second sensor 124 may comprise any suitable force or pressure sensor or combination thereof. In the depicted embodiment, first sensor 122 and second sensor 124 each comprise a single sensor, but one or both may be supplemented by one, two, or more additional sensors. Some examples of suitable sensors that may be used include force sensitive resistors, force sensitive capacitors, piezoelectric sensors, strain gauges, load cells, or other force or pressure sensors as known to those of skill in the art. In one embodiment, first sensor 122 may comprise a force sensitive resistor and second sensor 124 may comprise a force sensitive resistor. In the depicted embodiment, first sensor 122 and second sensor 124 are generally circular. However, other geometries may be used, such as rectangular or oval, to ensure appropriate contact with the femoral component of the knee prosthesis over the full range of motion of the knee. The sensors described above may be one, two, or more ribbon-type sensors and may be connected by direct wire or other equivalent means to the display portion.

In some embodiments, display portion 200 provides a user of knee ligament balancer 10 a visualization of the knee joint forces measured by sensor portion 100. Display portion 200 comprises a housing 210 containing a display 220 and a controller 230. Controller 230 is configured to receive the signals generated by first and second sensors 122, 124 to determine first and second force values and to control display 220 to provide a visual indication of the force measured by first sensor 122 and second sensor 124 on display 220. In some embodiments, the display 220 may comprise an LED, LCD, or other typical display as known to those of skill in the art. In some embodiments, display 220 may be touch-sensitive.

Figure 3A:
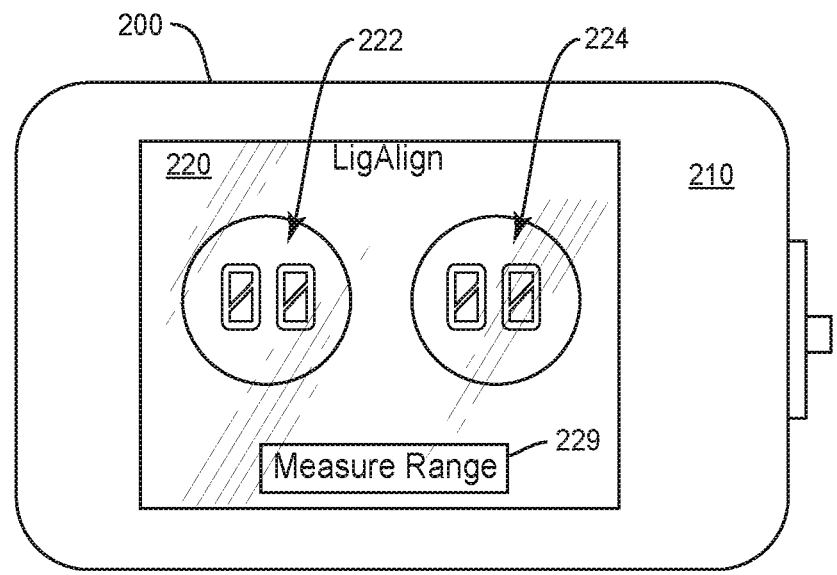
FIG. 3A illustrates a display of a representative knee ligament balancer showing a first visualization mode in accordance with the principles of the present disclosure.
Figure 3B:
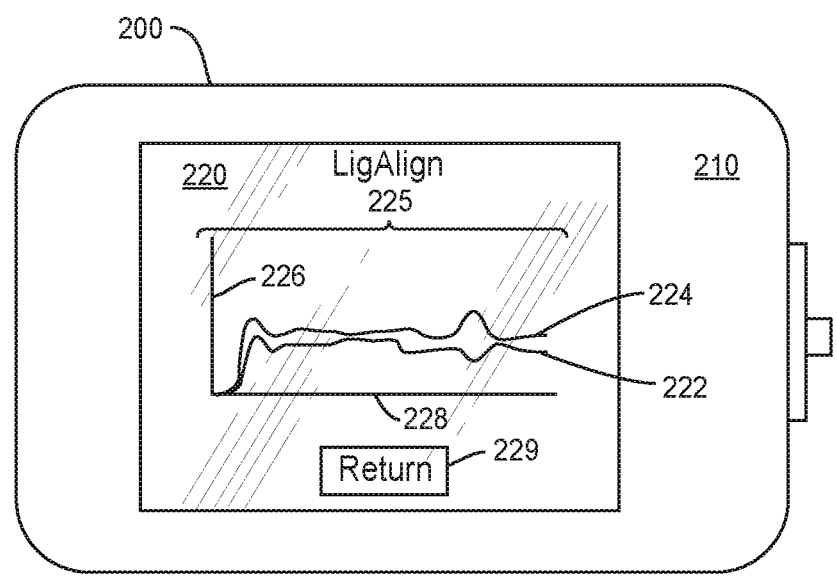
FIG. 3B illustrates a display of a representative knee ligament balancer showing a second visualization mode in accordance with the principles of the present disclosure.

The display 220 may provide a first visualization mode as shown in FIG. 3A. In the first visualization mode, a live reading of the first force value 222 and second force value 224 are depicted adjacent each other on the display 220. That is, the force values currently being measured by sensors 122, 124 are shown. In some embodiments, the depicted location of the force value is indicative of the sensor providing the displayed force value. That is, first force value 222, shown on the left of the display, corresponds to first sensor 122 within the left side of the sensor portion 100. Likewise, second force value 224, shown on the right of the display, corresponds to second sensor 124 within the right side of the sensor portion 100. This provides an intuitive way for a surgeon to easily orient the knee ligament balancer and understand the data being presented. In some embodiments, the display 220 may provide a second visualization mode wherein a plot 225 of the first force value 222 and the second force value 224 are displayed, as shown in FIG. 3B. The plot 225 may depict the force values on the y-axis 226, while the x-axis 228 may depict time, so that the first and second force values 222, 224 are recorded as a surgeon flexes and extends the knee joint. By utilizing the second visualization mode, a surgeon is provided with a recorded visual display of the first and second force values 222, 224 so that the full range of force values over the full range of motion of the knee may be easily seen and understood. In some embodiments, the x-axis 228 may depict the range of motion of the knee joint, e.g., from fully flexed to fully extended. In some embodiments, display portion 200 may allow the user to select between the first and second visualization modes. This may be through, e.g., a displayed button 229 if display 220 is a touch-sensitive display, or may be a hard-wired button provided in housing 210.

Figure 4:
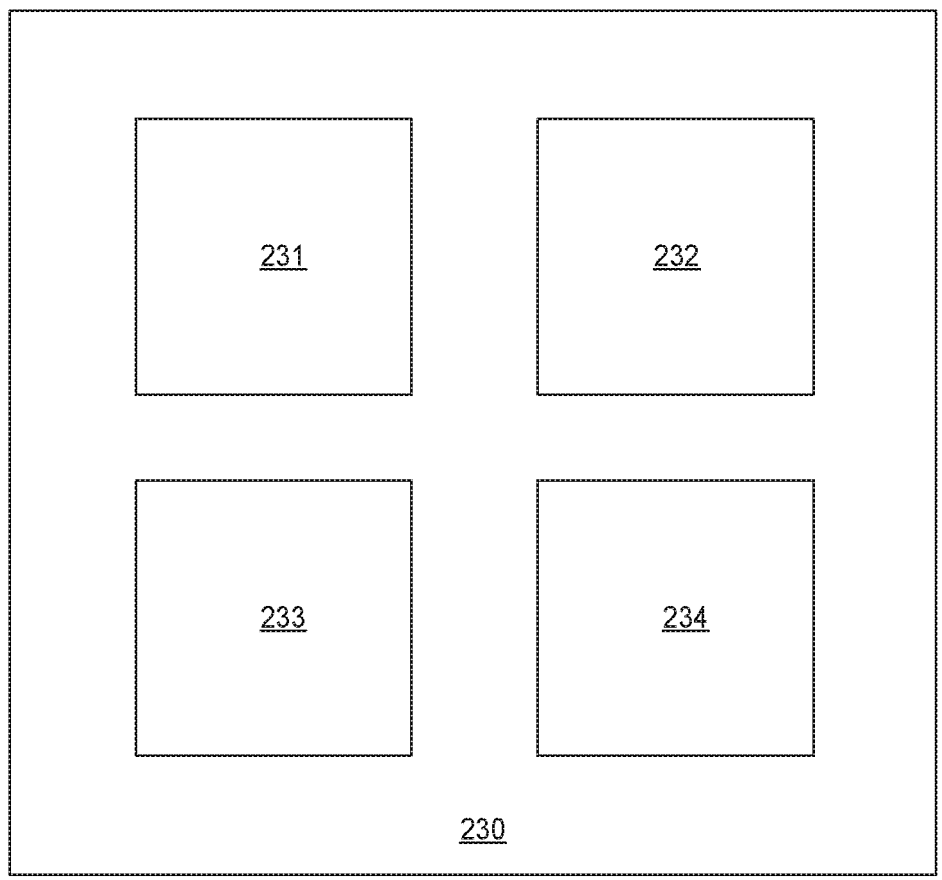
FIG. 4 is a functional block diagram of a controller of a representative knee ligament balancer in accordance with the principles of the present disclosure.

As shown in FIG. 4, controller 230 may be, for example, a typical integrated circuit board and comprise, e.g., a processor module 231, a memory module 232, a communication module 233, a power module 234, and/or other componentry as necessary to provide the functionality described herein. The processor module 231 may be embodied as any type of processor configured to perform the functions described herein. For example, the processor module 231 may comprise single or multi-core processor. The processor module 231 may be used to control display 210, or controller 230 may comprise a separate display module. The memory module 232 may be embodied as read-only memory devices and/or random access memory devices. For example, the memory device 232 may comprise electrically erasable programmable read-only memory devices (EEPROM), dynamic random access memory devices (DRAM), synchronous dynamic random access memory devices (SDRAM), double-data rate dynamic random access memory devices (DDR SDRAM), and/or other volatile or non-volatile memory devices. The communications module 233 receives the signals from sensor array 120 of sensor portion 100, and may comprise an analog-to-digital (A/D) to convert an analog voltage signal generated by sensor array 120 to a digital signal for processing and display by controller 230. The communications module 233 may also comprise circuitry or componentry to provide a wired or wireless connection between sensor portion 100 and display portion 200. Exemplary wired connections include, but are not limited to, a flexible flat cable (FFC) connection, a USB connection, a coaxial connection, an ethernet connection, or the like, and exemplary wireless connections include, but are not limited to, a BLUETOOTH connection, a radiofrequency connection, an infrared connection, a Z-wave connection, a ZIGBEE connection, or a wireless area network (WAN) connection. The power module 234 may comprise a power source and associated power control circuitry. In some embodiments, the power source may be one or more lithium ion battery cells or alternatively may be one or more thin film batteries such as, for example, lithium ion thin film batteries that may include encapsulation for added safety and containment of the battery materials and components. In other embodiments, the power source may be one or more AAA batteries. The power circuitry may include power control, distribution, and filtering circuitry and is configured to provide or distribute power from the power source to the other devices or components of controller 230. The various modules described herein, and/or others as may be necessary to provide the functionality described herein, may be communicatively coupled to transmit data, power, information, etc., via, e.g., wires, printed circuit board traces, bus, intervening devices, etc.

In some embodiments, connection wire 300 connects sensor portion 100 to display portion 200 and transmits the signals generated by sensor array 120 of sensor portion 100 to be received and processed by controller 230 of display portion 200. Exemplary wired connections include, but are not limited to, a flexible flat cable (FFC) connection, a USB connection, a coaxial connection, an ethernet connection, or the like. In the depicted embodiment, connection wire 300 may comprise a connector 310 disposed within a section of connection wire 300 such that the sensor portion 100 is detachable from the display portion 200. In other embodiments, connection wire 300 may comprise one or more connectors disposed on the ends of connection wire 300 such that sensor portion 100 is detachable from connection wire 300, display portion 200 is detachable from connection wire 300, or both sensor portion 100 and display portion 200 are detachable from connection wire 300. By providing that sensor portion 100 and/or display portion 200 may be detachable from each other and/or connection wire 300, different components of knee ligament balancer 10 may be configured for single-usage or may be configured to be reusable via an autoclaving procedure or the like.

In some embodiments, connection wire 300 may not be present, and sensor portion 100 may be connected wirelessly with display portion 200. Exemplary wireless connections include, but are not limited to, a BLUETOOTH connection, a radiofrequency connection, an infrared connection, a Z-wave connection, a ZIGBEE connection, or a wireless area network (WAN) connection.

Also provided herein is a method for performing an orthopedic surgical procedure on a knee joint of a patient using a knee ligament balancer 10 as described above. In a first step, a surgeon would adhere the tibial side 112 of the sensor portion 100 to a component of a knee prosthesis system, e.g., a trial insert. The surgeon then inserts the component of the knee prosthesis system with the sensor portion 100 of knee ligament balancer 10 attached thereto into the knee joint of a patient, wherein the first sensor 122 may be positioned within the medial compartment of the knee and the second sensor 124 may be positioned within the lateral compartment of the knee (or vice versa). Once in place, the surgeon may measure the forces within the medial and lateral compartments of the knee, with the force values being shown on display 220. In some embodiments, the forces of the lateral compartment and the medial compartment are measured over the full range of motion of the knee joint of the patient. In response to the measured force values of the lateral compartment and the medial compartment over the full range of motion of the knee joint of the patient, the surgeon may perform a balancing procedure to adjust the mediolateral balance of the knee joint of the patient.

It will be understood that various modifications may be made to the embodiments disclosed herein. Other embodiments will be apparent to those skilled in the art from consideration of the specification and practice of the embodiments disclosed herein. It is intended that the specification and examples be considered as exemplary only, with the true scope and spirit of the embodiments disclosed herein being indicated by the following claims.

What is claimed is:

1. An orthopedic surgical device comprising:
a sensor portion including a conformable pad sized for positioning within a knee joint of a patient, wherein the pad includes a femoral side, a tibial side, and a sensor array disposed between the femoral side and the tibial side configured to generate at least one signal indicative of a force within the knee joint, wherein the tibial side includes an adhesive coating; and
a display portion including a display and a controller, wherein the controller is configured to receive the signal from the sensor array and to control the display to provide a visual indication of the force within the knee joint.

2. The orthopedic surgical device of claim 1, further comprising a connection wire between the sensor portion and the display portion configured to transmit the signal to the controller.

3. The orthopedic surgical device of claim 2, wherein the connection wire comprises a connector such that the sensor portion is detachable from the display portion.

4. The orthopedic surgical device of claim 1, wherein the pad comprises a medical grade moldable plastic.

5. The orthopedic surgical device of claim 4, wherein the medical grade moldable plastic is silicon.

6. The orthopedic surgical device of claim 4, wherein the medical grade moldable plastic is polyurethane.

7. The orthopedic surgical device of claim 1, wherein the sensor array comprises a first sensor positioned laterally adjacent a second sensor.

8. The orthopedic surgical device of claim 7, wherein when the pad is positioned within the knee joint of the patient, the first sensor is positioned to generate a first signal indicative of a force within the lateral compartment of the knee joint and the second sensor is positioned to generate a second signal indicative of a force within the medial compartment of the knee.

9. The orthopedic surgical device of claim 8, wherein the controller is further configured to receive the first signal from the first sensor to determine a first force value and the second signal from the second sensor to determine a second force value and to control the display to provide a first visualization mode wherein the first force value is displayed adjacent the second force value.

10. The orthopedic surgical device of claim 9, wherein the controller is further configured to receive the first signal from the first sensor to determine a first force value and the second signal from the second sensor to determine a second force value and to control the display to provide a second visualization mode wherein a plot of the lateral force value and medial force value is displayed.

11. The orthopedic surgical device of claim 10, wherein the display portion is configured to allow a user of the orthopedic surgical device to switch between the first visualization mode and the second visualization mode.

12. The orthopedic surgical device of claim 8, wherein the controller is further configured to receive the first signal from the first sensor to determine a first force value and the second signal from the second sensor to determine a second force value and to control the display to provide a first visualization mode wherein a plot of the first force value and second force value is displayed.

13. The orthopedic surgical device of claim 7, wherein the first sensor comprises a force sensitive resistor and the second sensor comprises a force sensitive resistor.

14. The orthopedic surgical device of claim 7, wherein the first sensor comprises a circular, rectangular, or oval geometry, and the second sensor comprises a circular, rectangular, or oval geometry.

15. The orthopedic surgical device of claim 1, wherein the adhesive coating is an acrylate-based adhesive.

16. The orthopedic surgical device of claim 1, wherein the femoral side of the sensor portion is treated to increase lubricity compared to the tibial side of the sensor portion.

17. An orthopedic surgical device comprising:
a sensor portion including a conformable pad to be positioned within a knee joint of a patient, wherein the sensor portion includes a femoral side, a tibial side, and a sensor array disposed between the femoral side and the tibial side, wherein the sensor array includes a first sensor positioned laterally adjacent a second sensor such that when the pad is positioned within the knee joint of the patient, the first sensor is positioned to generate a first signal indicative of a force within the lateral compartment of the knee and the second sensor is positioned to generate a second signal indicative of a force within the medial compartment of the knee, wherein the tibial side includes an adhesive coating;
a display portion including a display and a controller, wherein the controller is configured to receive the first signal from the first sensor to determine a first force value and the second signal from the second sensor to determine a second force value and to control the display to provide a first visualization mode and a second visualization mode and a visual button to switch between the first visualization mode and the second visualization mode, wherein in the first visualization mode, the first force value is displayed adjacent the second force value and in the second visualization mode, a plot of the lateral force value and medial force value is displayed; and
a detachable connection wire between the sensor portion and the display portion configured to transmit the first signal and second signal to the controller.

18. A method for performing an orthopedic surgical procedure on a knee joint of a patient, the method comprising:
providing an orthopedic surgical device comprising:
a sensor portion including a conformable pad to be positioned within a knee joint of a patient, wherein the sensor portion includes a femoral side, a tibial side, and a sensor array disposed between the femoral side and the tibial side, wherein the sensor array includes a first sensor positioned laterally adjacent a second sensor such that when the pad is positioned within the knee joint of the patient, the first sensor is positioned to generate a first signal indicative of a force within the lateral compartment of the knee and the second sensor is positioned to generate a second signal indicative of a force within the medial compartment of the knee, wherein the tibial side includes an adhesive coating;
a display portion including a display and a controller, wherein the controller is configured to receive the first signal from the first sensor to determine a first force value and the second signal from the second sensor to determine a second force value and to control the display to provide a first visualization mode and a second visualization mode and a visual button to switch between the first visualization mode and the second visualization mode, wherein in the first visualization mode, the first force value is displayed adjacent the second force value and in the second visualization mode, a plot of the lateral force value and medial force value is displayed; and
a detachable connection wire between the sensor portion and the display portion configured to transmit the first signal and second signal to the controller,
adhering the tibial side of the pad to a component of a knee prosthesis system, inserting the component of the knee prosthesis system into the knee joint of the patient, and
measuring the forces of the lateral compartment and the medial compartment, wherein the forces are displayed on the display of the orthopedic surgical device.

19. The method of claim 18, wherein the forces of the lateral compartment and the medial compartment are measured over the full range of motion of the knee joint of the patient.

20. The method of claim 19, further comprising performing a balancing procedure to adjust a mediolateral balance of the knee joint of the patient.

\* \* \* \* \*